(12) United States Patent
Zech et al.

(10) Patent No.: US 6,193,722 B1
(45) Date of Patent: Feb. 27, 2001

(54) HOLLOW MILLING TOOL

(75) Inventors: Manfred Zech, Andelfingen; Alain Favre, Zürich, both of (CH)

(73) Assignee: Sulzer Orthopaedic AG, Baar (CH)

( * ) Notice: Subject to any disclaimer, the term of this patent is extended or adjusted under 35 U.S.C. 154(b) by 0 days.

(21) Appl. No.: 09/389,156

(22) Filed: Sep. 2, 1999

(30) Foreign Application Priority Data

Sep. 29, 1998 (EP) .................................................. 98810978

(51) Int. Cl.⁷ .................................................. A61B 17/00
(52) U.S. Cl. .................................................. 606/79; 606/80
(58) Field of Search .................................. 606/79, 80, 86, 606/96; 408/207, 201, 204, 226, 227, 228, 229, 212, 209

(56) References Cited

U.S. PATENT DOCUMENTS

| | | | |
|---|---|---|---|
| 4,649,918 | * | 3/1987 | Pegg et al. .............................. 606/79 |
| 5,205,685 | * | 4/1993 | Herbert .................................. 408/207 |
| 5,556,399 | * | 9/1996 | Huebner .................................. 606/80 |
| 5,873,684 | * | 2/1999 | Flolo ..................................... 408/222 |
| 5,921,987 | * | 7/1999 | Stone ..................................... 606/80 |
| 6,012,881 | * | 1/2000 | Scheer .................................. 408/227 |

FOREIGN PATENT DOCUMENTS

| | | | |
|---|---|---|---|
| 611624 | * | 8/1994 | (EP) ...................................... 606/79 |
| 824893 | * | 2/1998 | (EP) ...................................... 606/79 |

* cited by examiner

*Primary Examiner*—Pedro Philogene
(74) *Attorney, Agent, or Firm*—Townsend and Townsend and Crew LLP

(57) ABSTRACT

A hollow milling tool (1) for the production of substantially hollow cylindrical depressions in human or animal tissue, in particular for the production of tissue pillars which are removed at a harvest location, transported to a defect location and implanted there, has teeth (2) for the ablation of tissue which are arranged at the distal end of the milling tool at the end side. Furthermore, the milling tool has passages for transporting a cooling fluid to a cooling region of the milling tool lying near the distal end during the ablation of tissue.

11 Claims, 2 Drawing Sheets

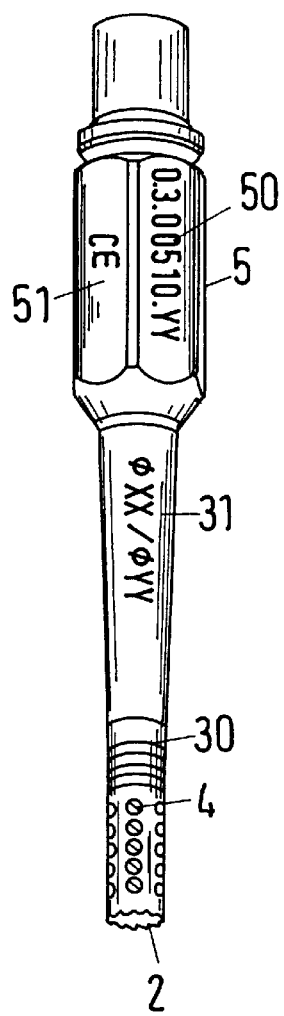
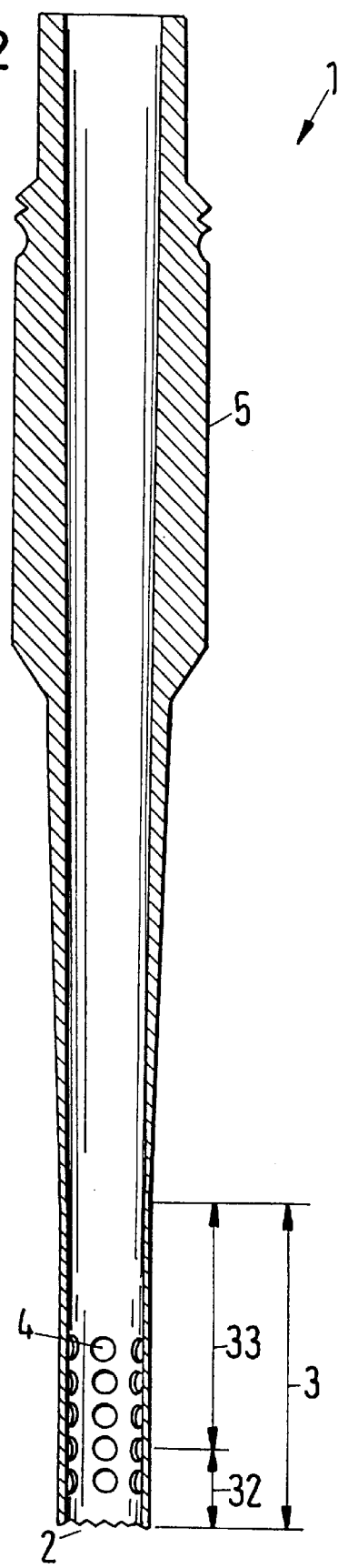

HOLLOW MILLING TOOL

BACKGROUND OF THE INVENTION

The invention relates to a hollow milling tool in accordance with the preamble of the independent patent claim.

Hollow milling tools of this kind are used for example in the transplantation of tissue pillars. For example cartilage defects are in certain cases nowadays "repaired" at stressed locations, such as e.g. joints, in such a manner that a blind bore is produced at the defect. location which reaches into the subchondral bone. At a less stressed harvest location then a tissue pillar is taken out which consists of bone which is covered with healthy cartilage. This tissue pillar is transported to the defect location and implanted there into the blind bore.

Various instruments have been proposed for the production of the tissue pillar at the harvest location such as e.g. punches or hollow milling tools (in some cases also designated as "crown borers"). A hollow borer of this kind has teeth which are arranged at the front side and which ablate the tissue in the production of the tissue pillar. The ablated tissue can be transported away through the inner space of the hollow milling tool or via the space which surrounds the hollow milling tool.

Bone tissue is ablated in the production of the tissue pillar. In this the tissue heats up in the immediate vicinity of the distal end of the milling tool (chip forming method). On the other hand, the bone tissue contains materials such as e.g. proteins which can stand only a very limited temperature increase because they could otherwise denature. In this, both tissue which is arranged directly outside round about the milling tool can be affected by a temperature increase of this kind as well as tissue which is directly surrounded by the milling tool, thus the tissue pillar or at least parts thereof.

SUMMARY OF THE INVENTION

An object of the invention is thus to propose a hollow milling tool in which it is ensured that neither the tissue directly surrounding the milling tool at the harvest location nor that of the tissue pillar can be damaged in the production and the removal of the tissue pillar.

This object is satisfied with the help of a hollow milling tool such as is characterised by the features of the independent patent claim. Advantageous embodiments of the hollow milling tool in accordance with the invention result from the features of the subordinate claims.

This object is satisfied in accordance with the invention by providing the hollow milling tool with means for the cooling of the region of the milling tool lying near the distal end during the ablation of tissue. Through this it is avoided that the milling tool can reach a temperature which can damage the tissue in that region with which it comes into contact with the tissue.

In one exemplary embodiment the means for the cooling can comprise discrete passage bores which are formed in the wall of the milling tool near the distal end. This is a particularly simple constructional measure.

In this a plurality of passage bores can be arranged in the wall of the milling tool at a uniform mutual spacing when viewed in the peripheral direction. Viewed in the axial direction a plurality of layers of passage bores of this kind, which are uniformly mutually spaced when viewed in the peripheral direction, can be provided in the wall of the milling tool.

In another exemplary embodiment the means for the cooling can comprise at least one groove which extends in spiral shape in the outer wall of the milling tool, and the orientation of which can be opposite to the direction of rotation during the ablation of tissue so that during the ablation a coolant, e.g. a physiological salt solution, can arrive through the groove at the distal end of the milling tool. Thus in this exemplary embodiment a (body compatible) coolant is actively supplied. Through the fact that the orientation of the spiral-shaped groove is opposite to the direction of rotation during the ablation of tissue, the supplied coolant can also arrive at the location where the cooling is to take place, namely at the region near the distal end of the milling tool, where the milling tool comes into contact with the tissue. The supplied coolant can be transported off through the inner space of the hollow milling tool together with the ablated tissue.

In a further exemplary embodiment of the hollow milling tool in accordance with the invention the cutting teeth which are arranged at the front side are conically outwardly sharpened to a point in the direction towards the distal end of the hollow milling tool starting at the inner wall or vice versa (i.e. they are sharpened to a point from the outside inwardly). Through this it is achieved that the milling tool can not slide off even when it is not applied exactly orthogonally to the cut surface.

The tips of the cutting teeth, which are arranged at the front side, can be rounded off (preferably with a very small radius), through which the lifetime of the cutting teeth is increased.

In the region of the distal end of the milling tool the inner diameter can at first be constant and then enlarge when viewed in the proximal direction. The outer diameter can in the region of the distal end of the milling tool also first remain constant and then decrease when viewed in the proximal direction. After the tissue pillar has been produced the hollow milling tool must be taken out again while the tissue pillar is still anchored at its base at the harvest location. It is then separated at its base with a suitable extractor and can then be taken out and transported to the defect location. The two described measures now serve to facilitate this removal of the hollow milling tool, but they can also be present in combination. If the inner diameter in the region of the distal end is first constant and then enlarges when viewed in the proximal direction, this means that the tissue pillar is still in contact with the inner wall of the hollow milling tool only at its distal end. Through this the hollow milling tool can be taken out more easily than if the tissue pillar were in contact with the inner wall of the hollow milling tool over its entire length. The same holds for the contact with the surrounding tissue. The hollow milling tool is now only in contact with the surrounding tissue at the distal end because the outer diameter of the hollow milling tool then decreases when viewed in the proximal direction. This likewise facilitates the removal of the hollow milling tool. In this it should be observed that it is a matter of only a slight change of the diameter here because the wall thickness of the hollow milling tool, which is not arbitrarily large anyway, cannot be arbitrarily reduced; quite considerable forces must be nonetheless transmitted to the cut surface during the milling of the subchondral bone.

Markings can be provided on the outer wall in the region of the distal end of the hollow milling tool which indicate to the surgeon or orthopedist the respective current penetration depth of the hollow milling tool and make it easier for him to produce a tissue pillar of a precisely determined length.

Furthermore, markings can be provided on the outer wall of the milling tool which contain other information on the milling tool (e.g. milling tool inner diameter, milling tool outer diameter, etc.). These are however preferably placed in a region different from that of those markings which indicate the current penetration depth of the hollow milling tool.

Further advantageous embodiments result from the description of the following exemplary embodiments of the hollow milling tool in accordance with the invention with reference to the drawings.

BRIEF DESCRIPTION OF THE DRAWINGS

FIG. 1 shows an exemplary embodiment of the hollow milling tool in accordance with the invention in a perspective view, FIG. 2 shows the exemplary embodiment of the hollow milling tool of FIG. 1 in a longitudinal section.

DESCRIPTION OF THE PREFERRED EMBODIMENTS

Figure 3:
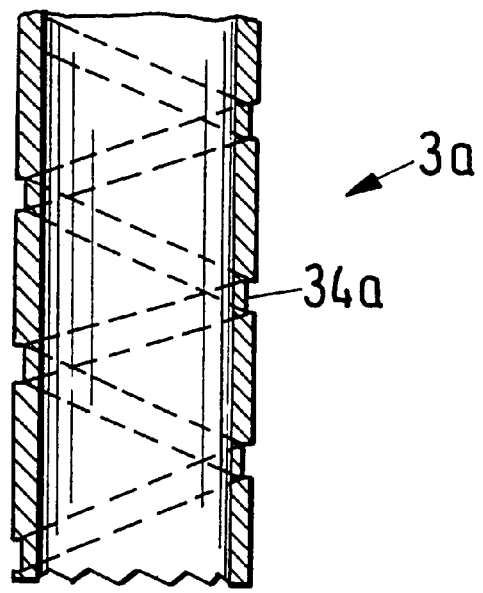
FIG. 3 shows the region of the distal end of a further exemplary embodiment of the hollow milling tool in accordance with the invention.

The exemplary embodiment of the hollow milling tool 1 in accordance with the invention which is illustrated in an (enlarged) longitudinal section in FIG. 2 allows it to be recognized that the hollow milling tool 1 has teeth 2 which are arranged at the front side at the distal end. In a region 3 near the distal end the hollow milling tool 1 is provided with discrete passage bores 4 in its wall. Here a plurality of passage bores 4 are provided when viewed in the peripheral direction and when viewed in the axial direction a plurality of layers of passage bores 4 of this kind which are mutually uniformly spaced in the peripheral direction are provided. These passage bores effect a cooling of the hollow milling tool 1 in the region 3 near the distal end, since there the hollow milling tool comes into contact with the tissue.

In the proximal region the hollow milling tool has a region 5 which is designed as a hexagon and which can be received in a chuck (not shown) of a conventional rotary drive (surgical drill) and clamped in so that the hollow milling tool can be driven rotationally by this rotary drive.

As one recognizes in FIG. 1, various markings can be placed on the outer wall of the hollow milling tool (e.g. through laser inscription). In the region 3 these can be markings 30 which indicate the penetration depth of the hollow milling tool 1 to the surgeon or the orthopedist. These markings 30 can be provided up to the distal end on the outer wall, that is, in particular also in the regions between passage bores 4 which are adjacent in the peripheral direction. For reasons of greater clarity this has been dispensed with in FIG. 1 however. Markings 31 can be provided at the proximal portion of the tool which give (coded or uncoded) information on the outer diameter and the inner diameter in the region of the distal end region of the hollow milling tool 1. In the region 5, which is formed as a hexagon, these can also include manufacturer specific information 50 (manufacturer serial numbers, type numbers, etc.) or else certification marks 51.

Furthermore, in the region 3 near the distal end of the hollow milling tool 1 the inner diameter can be at first constant (region 32) and then enlarge slightly (region 33). This can practically not be recognized in FIG. 2 because the enlargement of the inner diameter cannot be arbitrary, since the wall thickness of the hollow milling tool can not be arbitrary; forces which are required for the milling must nonetheless be transferred to the cut surface. The purpose of the enlargement of the inner diameter in region 33 is that the tissue pillar has contact with the inner wall of the hollow milling tool 1 only in the region 32 so that the hollow milling tool can be taken out more easily after the termination of the milling process.

For the same purpose the outer diameter in the region 3 near the distal end of the hollow milling tool 1 can at first be constant (region 32) and then decrease slightly. This as well can practically not be recognized in FIG. 2 for the reasons already named above. Both measures can be present in combination or only one of the measures.

The region 3a near the distal end of a further exemplary embodiment of the hollow milling tool in accordance with the invention is illustrated in FIG. 3. One recognises here that the means for the cooling comprise a groove 34a which extends in spiral shape in the outer wall of the hollow milling tool (of course a plurality of spiral-shaped grooves of this kind can also be provided). The orientation of this groove 34a is opposite to the direction of rotation of the milling tool during the ablation of tissue. Thus when the milling tool ablates tissue here when running to the right, then the groove 34a is oriented in the left direction of rotation.

This has as a result that during the milling a coolant, for example a physiological salt solution, can be conducted through this groove 34a to the distal end of the milling tool. The milling tool can thus be cooled in the distal end region, where it has contact with the tissue.

Figure 4:
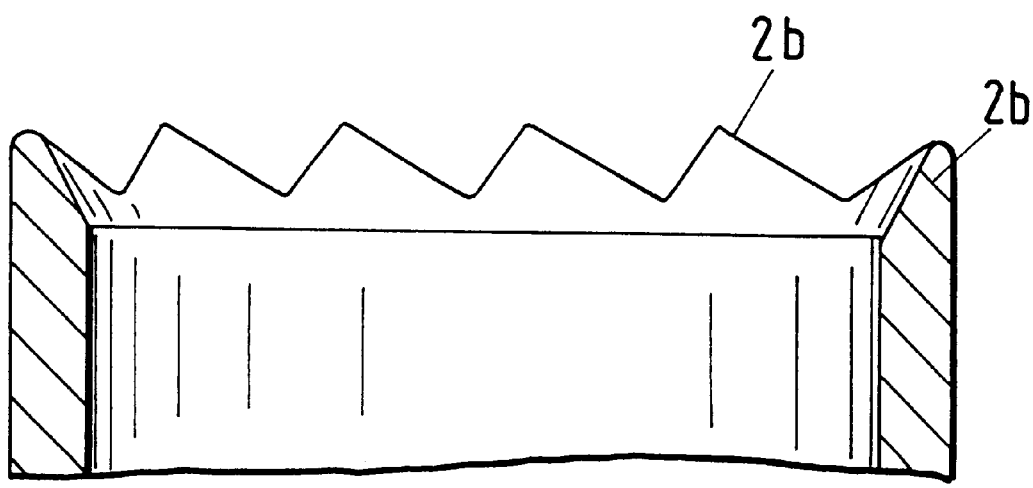
FIG. 4 shows an exemplary embodiment for the design of the endside teeth ("borer crown") of a hollow milling tool in accordance with the invention.

Finally, an exemplary embodiment of the design of the end-side cutting teeth 2b ("borer crown") is illustrated in FIG. 4. One recognizes here that starting from the inner wall the teeth 2b are outwardly sharpened to a point in the direction towards the distal end of the hollow milling tool. Through this it is achieved that when the hollow milling tool is not quite precisely placed orthogonally onto the tissue to be cut, it can nevertheless not slide off because the teeth 2b, which are sharpened to a point, hook in better into the tissue. In order to increase the lifetime of the teeth 2b, the teeth 2b can be rounded off at their tip with a very small radius.

As a material for milling tools of this kind, stainless steel comes under consideration, which can where appropriate be provided with a titanium nitride coating (TiN coating). The steel can also be heat treated, in particular hardened and/or quench aged. The milling tool can be sterilized and can therefore be reused after a cleansing and a subsequent sterilization.

What is claimed is:

1. A hollow milling tool for the production of substantially cylindrical depressions in human or animal tissue having
    a proximal end and a distal end;
    a plurality of teeth for an ablation of tissue, the teeth being arranged at the distal end of the milling tool; and
    a region being arranged at the distal end and extending in a proximal direction of the milling tool, said region comprising a cylindrical section extending from the teeth in the proximal direction as well as an enlarging section extending from a proximal end of the cylindrical section in the proximal direction, the cylindrical section having a constant inner diameter, and the enlarging section having an inner diameter which increases in the proximal direction.

2. The hollow milling tool of claim 1 including means for the cooling of the region during the ablation of tissue.

3. The hollow milling tool of claim 2 wherein the means for the cooling comprise discrete passage bores which are formed in a wall of the milling tool near the distal end.

4. The hollow milling tool of claim 3 characterized in that when viewed in a peripheral direction a plurality of discrete passage bores are arranged in the wall of the milling tool with a uniform mutual spacing; and in that when viewed in an axial direction a plurality of layers of discrete passage bores which are mutually uniformly spaced when viewed in the peripheral direction are provided in the wall of the milling tool.

5. The hollow milling tool of claim 2 characterized in that the means for the cooling comprise at least one groove which extends in spiral shape in an outer wall of the milling tool that has an orientation which is opposite to a direction of rotation of the tool during the ablation of tissue so that when tissue is being ablated a coolant can arrive through the groove at the distal end of the milling tool.

6. The hollow milling tool of claim 1 wherein the cylindrical section of the region has an outer diameter which is constant with respect to the proximal direction and the enlarging section of the region has an outer diameter which decreases in the proximal direction.

7. The hollow milling tool of claim 1 wherein the cylindrical section is defined by inner and outer wall surfaces, and wherein the teeth have pointed ends facing in the distal direction, the pointed ends being relatively proximate the outer wall surface and relatively remote from the inner wall surface of the cylindrical section.

8. The hollow milling tool of claim 1 wherein tips of the teeth, which are arranged at the distal end, are rounded off.

9. The hollow milling tool of claim 1 wherein markings are provided on an outer wall in the region at the distal end of the milling tool for the indication of a tool penetration depth.

10. The hollow milling tool of claim 1 with markings being provided on an outer wall of the milling tool which contain information on the milling tool.

11. A hollow milling tool for the production of substantially cylindrical depressions in human or animal tissue having a proximal end and a distal end;

a plurality of teeth for an ablation of tissue, the teeth being arranged at the distal end of the milling tool;

a region being arranged at the distal end and extending in a proximal direction of the milling tool, said region comprising a cylindrical section abutting the teeth and extending in the proximal direction as well as an enlarging section extending from a proximal end of the cylindrical section in the proximal direction, the cylindrical section having an inner diameter which is constant with respect to the proximal direction and the enlarging section having an inner diameter enlarging when viewed in the proximal direction; and a means for the cooling of the region at the distal end during the ablation of tissue.

* * * * *